(12) United States Patent
Amrani

(10) Patent No.: US 9,302,097 B2
(45) Date of Patent: Apr. 5, 2016

(54) IMPLANTABLE LEAD WITH TETHERS

(76) Inventor: Jacob Amrani, Scottsdale, AZ (US)

( * ) Notice: Subject to any disclaimer, the term of this patent is extended or adjusted under 35 U.S.C. 154(b) by 244 days.

(21) Appl. No.: 13/555,320

(22) Filed: Jul. 23, 2012

(65) Prior Publication Data

US 2013/0023974 A1 Jan. 24, 2013

Related U.S. Application Data

(60) Provisional application No. 61/510,724, filed on Jul. 22, 2011, provisional application No. 61/513,736, filed on Aug. 1, 2011, provisional application No. 61/601,122, filed on Feb. 21, 2012.

(51) Int. Cl.
*A61N 1/05* (2006.01)

(52) U.S. Cl.
CPC ............ *A61N 1/0553* (2013.01); *A61N 1/0558* (2013.01); *Y10T 29/49002* (2015.01)

(58) Field of Classification Search
CPC ..... A61N 1/05; A61N 1/0551; A61N 1/0558; A61N 1/057; A61B 5/042
USPC .................................... 607/117, 126; 600/37
See application file for complete search history.

(56) References Cited

U.S. PATENT DOCUMENTS

| | | |
|---|---|---|
| 4,549,556 A | 10/1985 | Tarjan et al. |
| 6,175,769 B1 | 1/2001 | Errico et al. |
| 2005/0004638 A1 | 1/2005 | Cross |
| 2005/0137672 A1* | 6/2005 | Coe et al. ....................... 607/126 |
| 2006/0161235 A1 | 7/2006 | King |
| 2007/0265691 A1* | 11/2007 | Swanson .............. A61N 1/0553 607/117 |
| 2008/0269861 A1* | 10/2008 | Cross ..................... A61N 1/056 607/116 |
| 2009/0099439 A1* | 4/2009 | Barolat .......................... 600/372 |
| 2010/0063568 A1* | 3/2010 | Staunton et al. ............... 607/116 |
| 2010/0070010 A1 | 3/2010 | Simpson |
| 2011/0071540 A1 | 3/2011 | Kast et al. |
| 2012/0029275 A1* | 2/2012 | Chu ................................ 600/37 |
| 2012/0203246 A1 | 8/2012 | Staunton et al. |
| 2013/0131766 A1* | 5/2013 | Crosby et al. .................. 607/116 |

* cited by examiner

*Primary Examiner* — Michael Kahelin
*Assistant Examiner* — Minh Duc Pham
(74) *Attorney, Agent, or Firm* — Alicia M. Passerin, Esq.; Pietragallo Gordon Alfano Bosick & Raspanti, LLP

(57) ABSTRACT

An implantable lead for electrical stimulation of a spinal cord is disclosed. The implantable lead has a paddle having a surface and a first and a second end, an electrode array positioned and arranged on the surface of the paddle, and at least one tether having an end that extends from one of the first and the second end of the paddle. The electrode array has at least one electrode contact configured to communicate with a corresponding electrode and a conductor. The implantable lead may be included in a kit that also has a securing device and instructions for implanting the implantable lead into the spinal cord. A method of making the implantable lead configured for electric stimulation of a spinal cord is also disclosed. A method of implanting the implantable lead in a spinal canal is also disclosed.

28 Claims, 6 Drawing Sheets

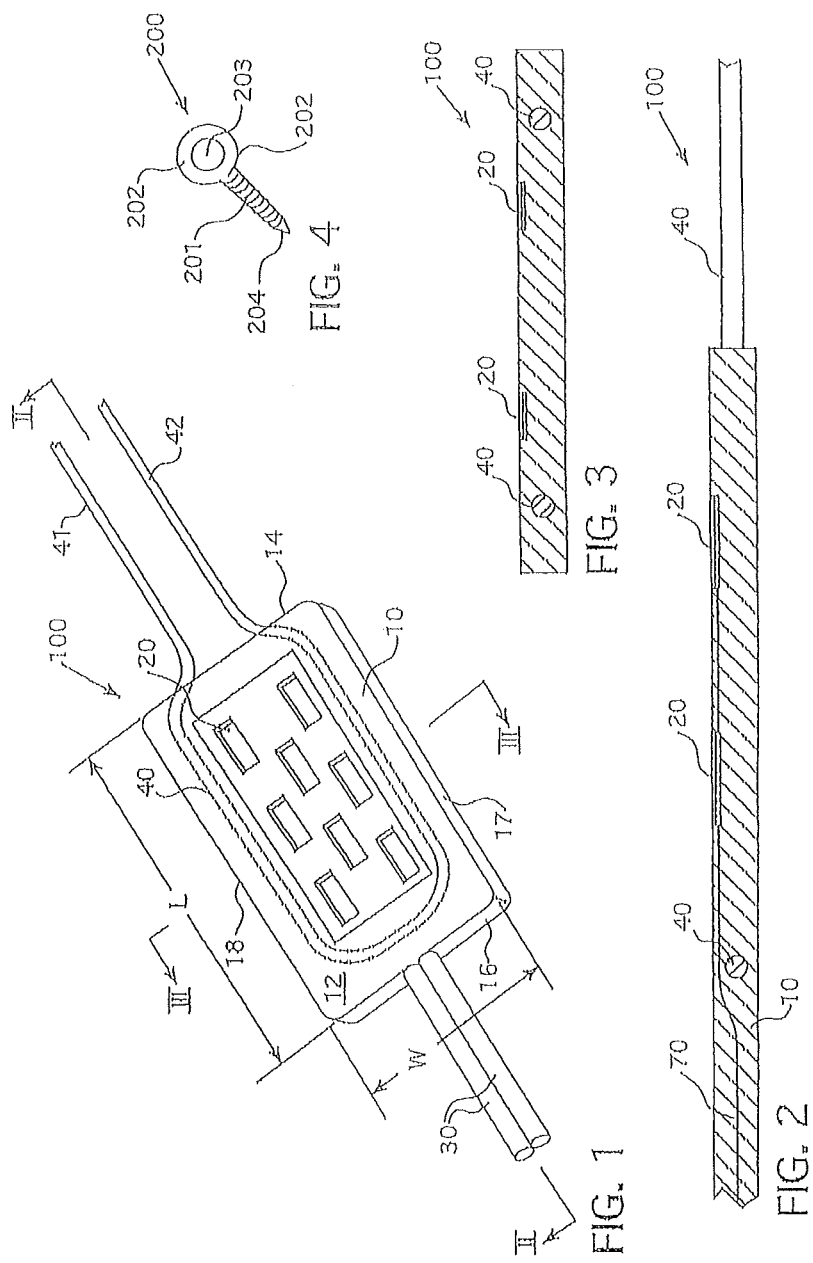

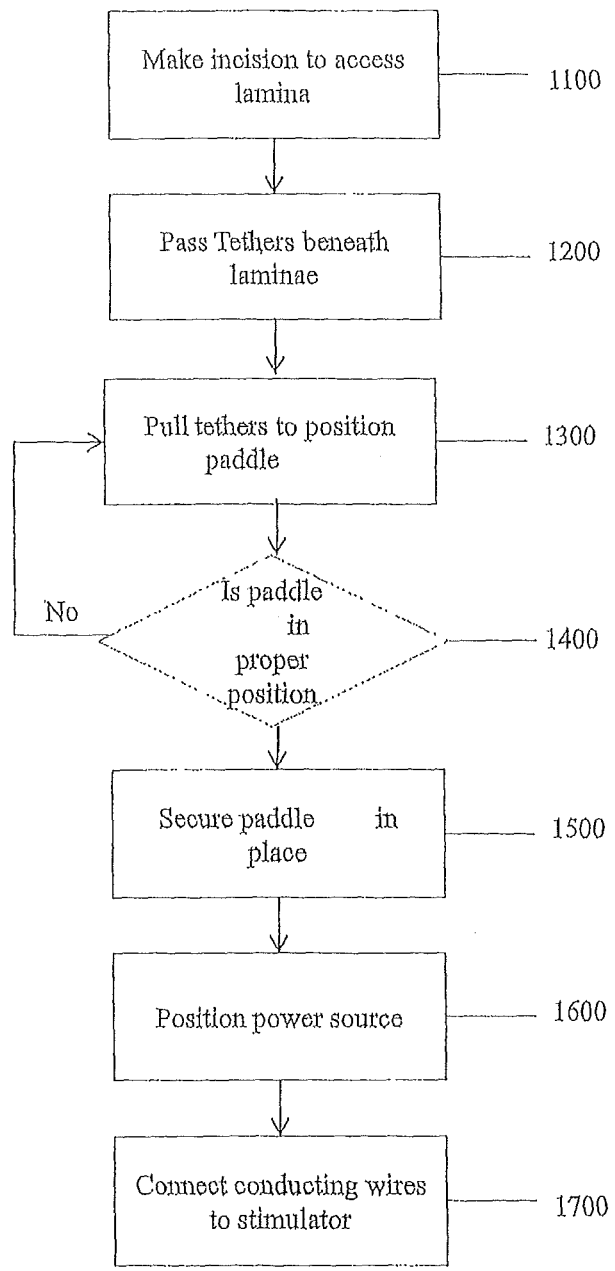

IMPLANTABLE LEAD WITH TETHERS

CROSS REFERENCE TO RELATED APPLICATIONS

This application claims priority to U.S. Provisional Application No. 61/510,724, filed Jul. 22, 2011, U.S. Provisional Application No. 61/513,736, filed Aug. 1, 2011, and U.S. Provisional Application No. 61/601,122, filed Feb. 21, 2012, all of which are incorporated herein by reference.

BACKGROUND

Most permanent stimulators for the management of chronic pain are implanted in the thoracic spine. The thoracic spine is different from the cervical and lumbar spine. In the cervical spine, the vertebrae are smaller and the canal is conical. The cervical and lumbar spine are more mobile and offer less shingling of the laminae than the thoracic spine. As such, implantation in these regions using conventional thoracic stimulators is challenging. Even in the thoracic spine, situations occasionally arise when conventional anchoring techniques are not appropriate.

SUMMARY

In an embodiment, an implantable lead for electrical stimulation of at least a portion of a spinal cord is disclosed. The implantable lead has a paddle having a surface and a first and a second end, an electrode array positioned and arranged on the surface of the paddle, and at least one tether having an end that extends from one of the first and the second end of the paddle. The electrode array has at least one electrode contact configured to communicate with a corresponding electrode and a conductor.

In another embodiment, an implantable lead for electric stimulation of at least a portion of a spinal cord is disclosed. The lead has a paddle having a surface and a distal end and a proximal end and an electrode array positioned and arranged on the surface of the paddle, and at least one tether is positioned a distance from an edge of the paddle, extending around a perimeter of the paddle, and having an end that extends from the distal end of the paddle. The electrode array has a plurality of electrode contacts each positioned in a recess formed below the surface of the paddle and configured to communicate with a corresponding electrode and a conductor.

In another embodiment, a method of making an implantable lead configured for electric stimulation of at least a portion of a spinal cord is disclosed. The method has the step of forming a paddle having a surface, an end, and at least one tether extending from the end, wherein an electrode array is positioned and arranged on the surface of the paddle. The electrode array has at least one electrode contact configured to communicate with a corresponding electrode and a conductor.

In another embodiment, a method of implanting an implantable lead in a spinal canal is disclosed. The implantable lead has a paddle having a surface and distal and proximal ends, an electrode array positioned and arranged on the surface of the paddle, and at least one tether having an end that extends from the distal end of the paddle. The electrode array has at least one electrode contact configured to communicate with a corresponding electrode and a conductor. The method of implanting has the steps of: exposing a portion of a spinal cord; passing a suture beneath at least one of a lamina or a portion of a spine at a position near the exposed portion of the spinal cord; pulling, using the suture, the tethers of the lead in a distal direction to insert the lead into an epidural space in the spinal canal; and securing, using the tethers, the lead in the epidural space.

In another embodiment, a kit that has an implantable lead for electrical stimulation of at least a portion of a spinal cord and instructions for implanting the implantable lead into a spinal canal is disclosed. The implantable lead has a paddle having a surface and a first and a second end, an electrode array positioned and arranged on the surface of the paddle, and at least one tether having an end that extends from one of the first and the second end of the paddle. The electrode array has at least one electrode contact configured to communicate with a corresponding electrode and a conductor. The kit may include a securing device that is configured to receive at least one of the ends of the tether.

Other objects, features, aspects and advantages of the paddle lead with tethers will become better understood or apparent from the following detailed description, drawings, and appended claims.

BRIEF DESCRIPTION OF THE FIGURES

In the drawings which are attached hereto and made a part of this disclosure:

FIG. 1 is a schematic top isometric view of an embodiment of a lead having a paddle with tethers;

FIG. 2 is a schematic of a cross-section of the lead depicted in FIG. 1 taken through line II-II;

FIG. 3 is a schematic of a cross-section of the lead depicted in FIG. 1 taken through line III-III;

FIG. 4 is a schematic isometric view of an embodiment of a securing device for use in connection with a lead such as the embodiment shown in FIG. 1;

FIG. 9 illustrates a flowchart of an embodiment of a method of implanting a stimulator that includes a lead such as the one illustrated in FIG. 1.

DETAILED DESCRIPTION

Figure 5:
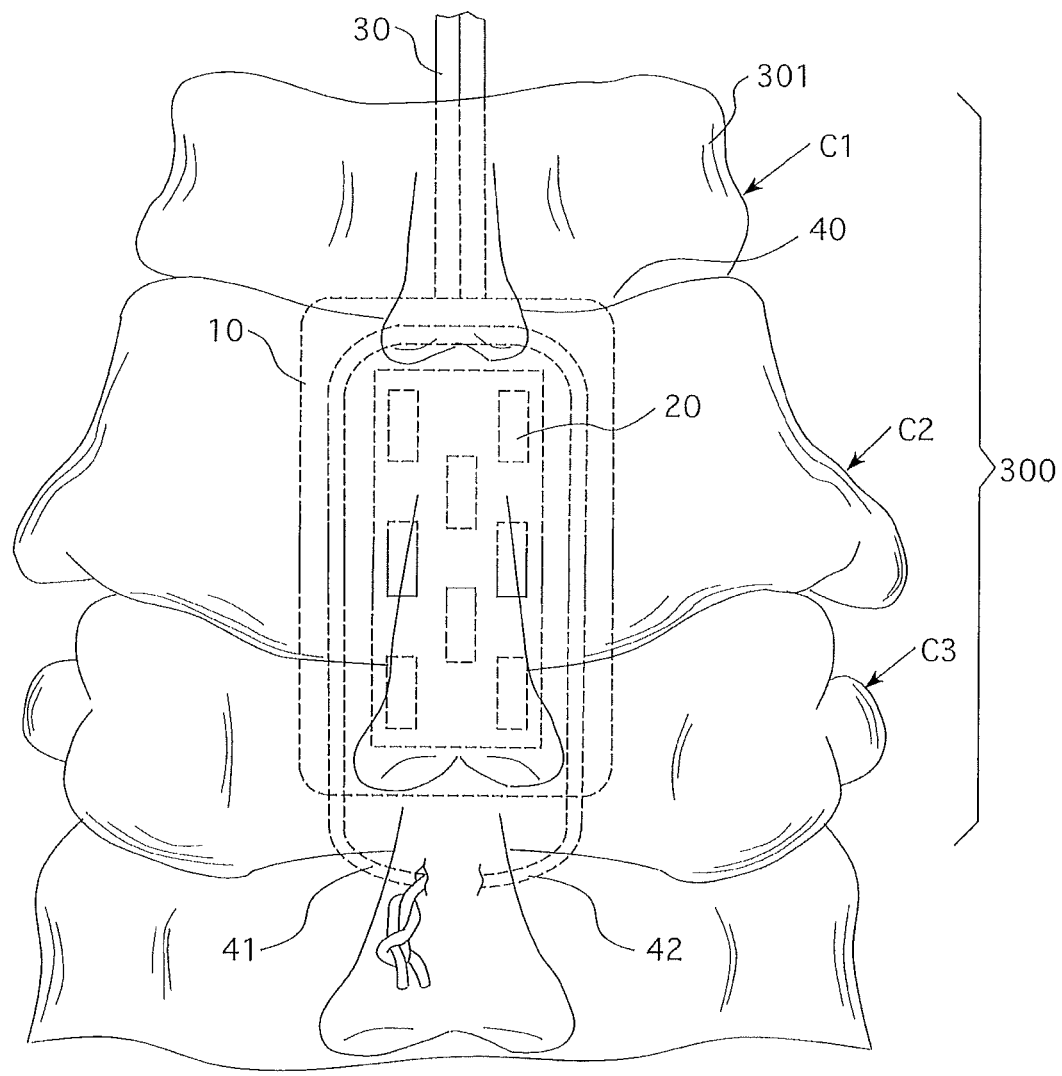
FIG. 5 is a schematic top view of the vertebral column from C1-C3 showing an embodiment of a lead positioned in the spinal canal retrograde over the ring of C1 and secured to C2.

In an embodiment, the present disclosure describes an implantable lead 100 for electrical stimulation of a spinal cord. In an embodiment, the lead 100 is configured to be implanted in a spinal canal at the region of the cervical spinal cord. In other embodiments, the lead 100 is configured to be implanted in the spinal canal at other regions of the spinal cord. As illustrated in FIGS. 1-3, the lead 100 comprises a paddle 10, an electrode array comprising at least one electrode contact 20 configured to communicate with a corresponding electrode (not shown) and a conductor 30 having wires that connect the electrodes to a power source (not shown). The lead 100 has at least one tether 40 that extends from a distal end 14 of the paddle 10.

As illustrated in FIGS. 2 and 3, the paddle 10 is generally flat, but may have a slight curve and has a surface 12 and distal 14 and proximal 16 ends. Referring to FIG. 1, the paddle 10 has distal and proximal edges 14a, 16a that define a length L and sides 17, 18 that define a width W. The paddle 10 may be configured such that the length L spans one vertebral level of the spinal cord. In embodiments, the width W of the paddle 10 ranges from about 7.5 mm to about 12.5 mm and the length L of the paddle 10 ranges from about 26.25 mm to about 43.75 mm. In embodiments, the paddle 10 has a thickness of about 1.5 mm to about 2.5 mm.

As illustrated in FIG. 1, the electrode array is positioned on or in a recess (not shown) formed below the surface 12 of the paddle. The electrode array comprises at least one electrode contact 20 that is configured to communicate with a corresponding electrode 70. Each electrode 70 is connected to a conductor or a conducting wire 30 that connects the electrode 70 to a power source (not shown) that transmits electric current for stimulation of the spinal cord. In the embodiment shown in FIGS. 1-3, the electrode array comprises eight electrode contacts 20 and eight corresponding electrodes 70 arranged in an array of rows and columns. In an embodiment such as the one illustrated in FIGS. 2 and 3, each electrode contact 20 is positioned in a recess formed below the surface 12 of the paddle 10. In an embodiment, each electrode contact 20 is substantially rectangular in shape.

Figure 6:
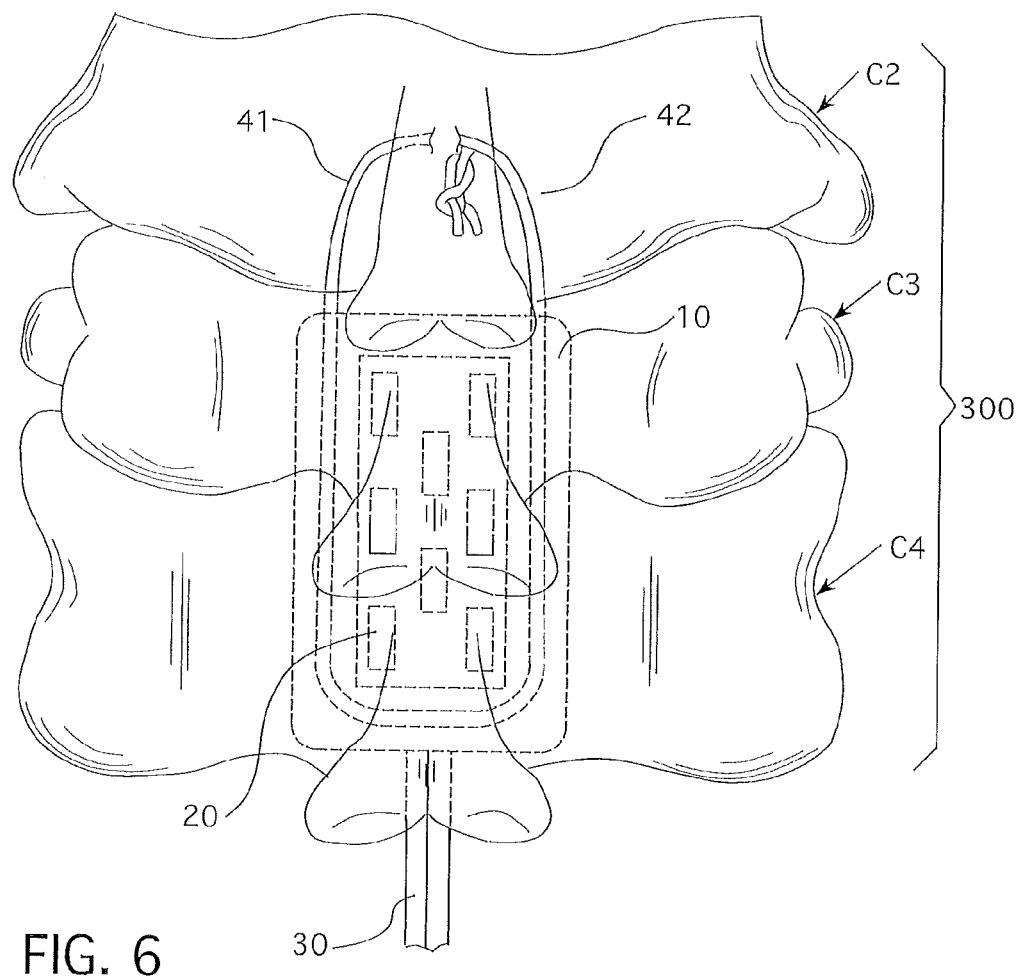
FIG. 6 is a schematic top view of the vertebral column from C2-C4 showing an embodiment of a lead inserted anterograde with the tethers to be tied into C2.
Figure 7:
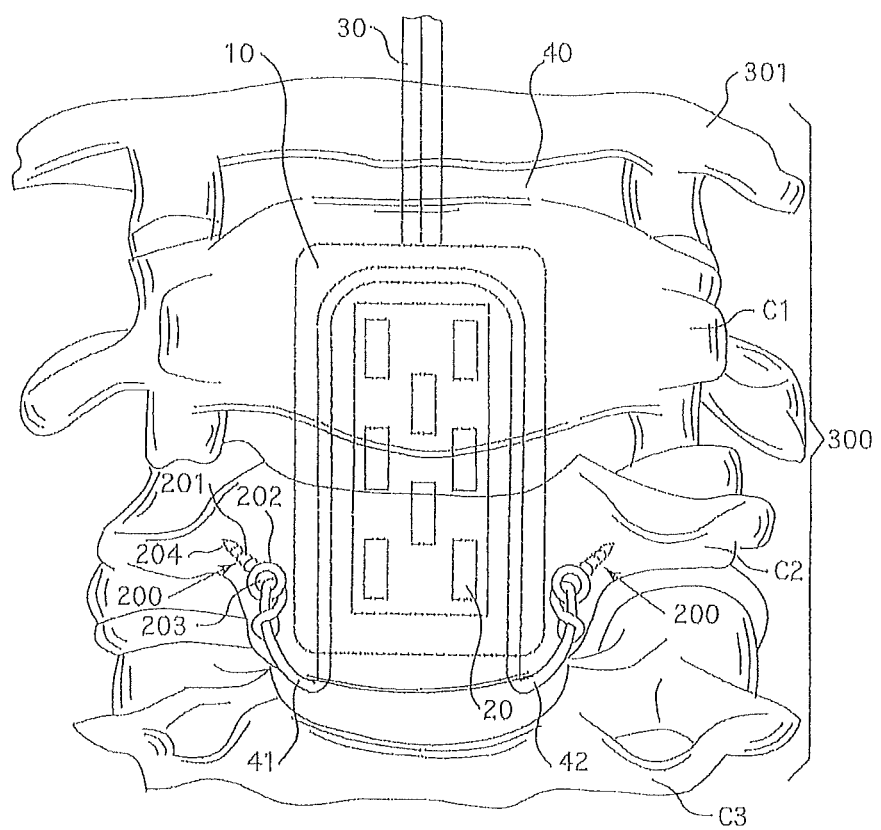
FIG. 7 is a schematic top view of the vertebral column from C1-C3 showing an embodiment of a lead positioned in the spinal canal retrograde over the ring of C1 and secured to C2 using a securing device.
Figure 8:
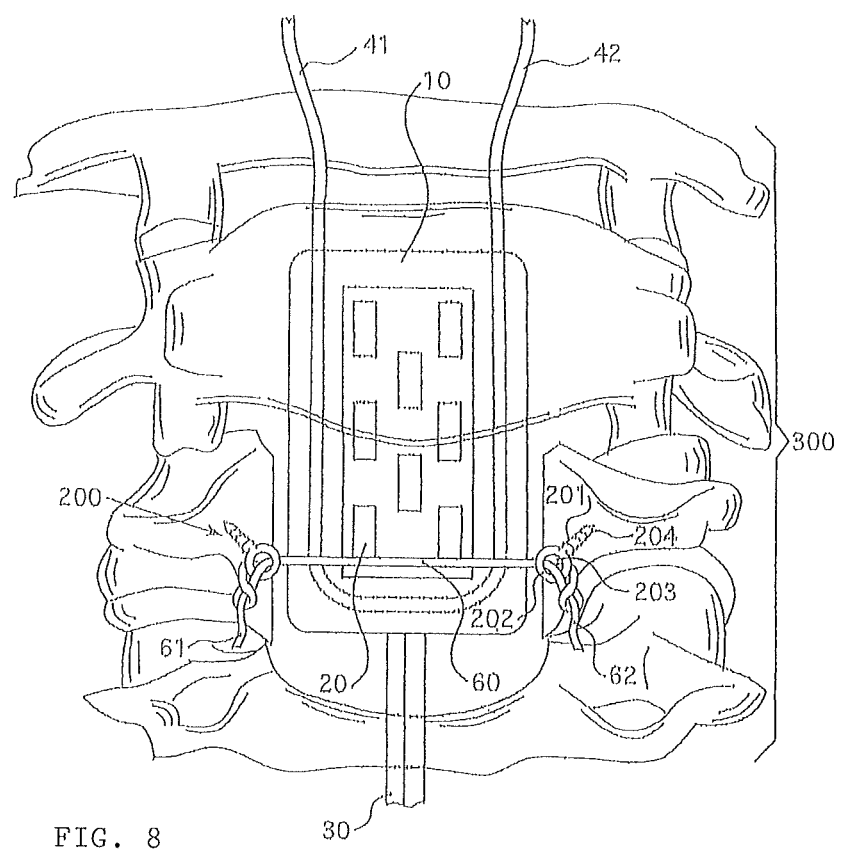
FIG. 8 is a schematic top view of the vertebral column from C1-C3 showing an embodiment of a lead inserted anterograde with the tethers to be tied into the cephalad vertebra using a securing device.

The lead 100 has a tether 40 as illustrated in FIGS. 1 to 3. In an embodiment (not shown), the tether 40 has a first end 41 that extends from one of the ends of the paddle 10. In another embodiment illustrated in FIGS. 1 and 3, the tether 40 has the first end 41 and a second end 42 that extend from one end of the paddle 10. In an embodiment, the tether 40 is integral with the paddle 10. In an embodiment such as the one illustrated in FIGS. 1 to 3, the tether 40 is embedded below the surface of the paddle. In an embodiment such as the one illustrated in FIGS. 1 to 3, the tether 40 substantially extends around a perimeter of the paddle 10 and is positioned a distance from an edge 14, 16 of the paddle 10. The tether 40 is substantially parallel to each edge 14, 16 and each side 17, 18. This positioning secures the tether 40 below the surface 12 of the paddle and minimizes the risk of tether 40 becoming disconnected from the paddle 10 during positioning of the lead 100 in the epidural space of the spinal canal. At least one end 41, 42 of the tether 40 extends from the distal edge 14 of the paddle 10. In the embodiment shown, first and second ends 41, 42 extend from the distal edge 14 of the paddle 10. In use, ends 41, 42 of tether 40 are inserted beneath the lamina to pull the lead 100 into the spinal canal and in an embodiment may be used to secure the lead 100 in place by direct attachment to a portion of the vertebral column (FIGS. 5 and 6) or by attachment to a securing device (FIGS. 7 and 8).

In another embodiment, a securing device 200 is disclosed. In an embodiment illustrated in FIG. 4, the securing device 200 comprises a head 202 having an opening 203 therein and a threaded cylindrical portion 201 having a tip 204. The head 202 is on a distal end of the cylindrical portion 201. The head 202 may be circular in shape to facilitate insertion of the ends 41, 42 of the tether or the ends 61, 61 of a suture (described below). In an embodiment, the securing device 200 is made from a biologically inert material that avoids scatter on a scan, such as titanium.

In use, the securing device 200 is used to secure an implantable lead such as the one illustrated in FIGS. 1 to 3 in the spinal canal. The tip 204 and at least a portion of the cylindrical portion 201 are inserted into a vertebra 300 such that a base 202' of the head 202 is substantially flush with a surface of the vertebra 300. In a first embodiment illustrated in FIG. 7, the lead 100 is positioned in the spinal canal at C1 and the securing device 200 is positioned at C2 such that the ends 41, 42 of the tether 40 are threaded through the opening 203 and are tied to the head 202 to secure the lead 100 in the spinal canal. In an alternate embodiment illustrated in FIG. 8, the lead 100 is positioned in the spinal canal at C1 and the securing device 200 is positioned at C2. A suture 60 having first and second ends 61, 62 is extended across a proximal portion of the paddle 10. Each end 61, 62 of the suture 60 is threaded through an opening 203 and is tied to the head 202 to secure the lead 100 in the spinal canal.

In another embodiment, a kit having the lead 100 (described above) and instructions for a method of implanting the lead 100 in the epidural space of the spinal canal (described below) is disclosed. The kit may include the securing device 200 (described above).

In an embodiment, a method of making an implantable lead 100 configured for electric stimulation of a spinal cord is disclosed. The method includes the step of forming a paddle 10 having a surface 12, distal and proximal ends 14, 16, and at least one tether 40 extending from an end 14, 16 as described above and shown generally in the figures. An electrode array is positioned and arranged on the surface 12 of the paddle 10. The electrode array has at least one electrode contact 20 configured to communicate with a corresponding electrode 70 and a conductor 30. In an embodiment such as the one shown in FIGS. 1 to 3, at least one recess is formed below the surface 12 of the paddle 10 and each electrode contact 20 is positioned in one of the recesses. In an embodiment, the at least one tether 40 may be integral with the paddle 10. In an embodiment, the tether 40 may embedded below the surface 12 of the paddle 10. In an embodiment such as the one illustrated in FIG. 1, the tether 40 substantially extends around a perimeter of the paddle 10 and is positioned a distance from an edge of the paddle 10.

In embodiments, the paddle 10 is made from silastic or any other biocompatible plastic. In embodiments, the tether 40 is made from a braided, nonabsorbable material. In an embodiment, the tether 40 is made from number zero ethibond suture.

In another embodiment illustrated in FIG. 9, a method 1000 of implanting an implantable lead 100 is disclosed. In a first step 1100, an incision is made in order to access the desired lamina.

Next, at step 1200, the tethers are passed beneath the laminae. The implantable lead may be positioned in any region of the spine. The tethers are passed antegrade and are used to anchor the lead to a cephalad spinous process or to a vertebra.

At step 1300, the lead is pulled in a direction by the tethers into the epidural space, with the distal edge of the paddle being oriented distally in the epidural space in order to position the lead in the epidural space.

At step 1400, proper positioning of the lead in the epidural space is confirmed, such as by x-ray. If necessary, step 1300 is repeated to adjust the position of the lead in the epidural space.

At step 1500, the lead is secured in place in the epidural space. In an embodiment, the lead is secured in the epidural space by tying the tethers directly to a spinous process or other part of a vertebra. In another embodiment, the lead is secured in the epidural space by inserting a securing device into a spinous process or other part of a vertebra and tying the tethers to the securing device.

At step 1600, a small incision is created over one of the buttocks and the power source is positioned beneath the skin.

At step 1700, the conducting wires are connected to the stimulator.

EXAMPLES

All procedures are performed under general anaesthesia. The patient is positioned prone on a radiolucent operating table with the head in a Mayfield horse shoe. The arms are tucked to the sides. A standard posterior approach to the spine is made. The spinous process of C2 is used as a landmark in the cervical region. For implantation over the ring of C1, the spine is exposed subperiosteally from the occiput to C3. For subaxial implantation of the lead, the spine is exposed from C2 to C5. For implantation in the thoracic or lumbar region, flouroscopy is used to identify the spinous process of the vertebral level to be implanted. A standard posterior approach is then made.

For patients with neck and arm pain, the lead is inserted antegrade under C4 and C3. After exposing the spine from C2 to C5, the inferior 2-3 mm of the spinous processes of C2, C3 and C4 are removed with a Leksell rongeur. A 1 or 2 mm Kerrison rongeur is then used to remove the ligamentum flavum at C2-3, C3-4 and C4-5. A 2-0 Ethibond suture on a CT-2 needle is passed backhand beneath the lamina of C4 from C4-5 to C3-4, and then beneath C3 from C3-4 to C2-3. The 2-0 Ethibond suture is used to pull the tethers under C4 and C3. The tethers are then used to guide the paddle under C4 and C3. A towel clip is used to create a hole in the spinous process of C2 or C3. A free needle is used to pass one tether through the spinous process hole, which is then tied to the other tether. No other anchoring is used, i.e., silastic sleeves are not used at all with this tethering technique.

For patients who have occipital or temporal pain, in addition to neck and arm pain, the tethered lead can be passed over the ring of C1. After exposing the spine from the occiput to C3, the ligamentum is removed from C1-C2 and occiput-C1. Different sized needles are used to pass sutures beneath the ring of C1 and the lamina of C2. These are used to pull a suture of 0 Ethibond from the top of C1 to the bottom of C2. The sublaminar suture is then used to pull the tethers first beneath C1, then beneath C2. The tethers are used to guide the paddle beneath C1 and C2. The tethers can then be tied around or through the spinous process of C2.

Implantation in the thoracic or lumbar spine is similar to the technique described for subaxial implantation after identifying and exposing the appropriate level.

While the foregoing has been set forth in considerable detail, it is to be understood that the drawings, detailed embodiments, and examples are presented for elucidation and not limitation. Design variations, especially in matters of shape, size, and arrangements of parts, may be made but are within the principles of the invention. Those skilled in the art will realize that such changes or modifications of the invention or combinations of elements, variations, equivalents, or improvements therein are still within the scope of the invention.

I claim:

1. An implantable lead for electrical stimulation of a spinal cord, comprising:
   a paddle sized to be positioned in the epidural space of the spinal canal and having a surface, a first and a second end, and a length that spans one vertebral level of the spinal cord;
   an electrode array positioned and arranged on the surface of the paddle, the electrode array comprising at least one electrode contact configured to communicate with a corresponding electrode and a conductor; and
   at least one tether having a portion that is connected to the paddle and an end that extends from and is unattached to one of the ends of the paddle, wherein the tether is configured to pull the paddle into the epidural space and secure the implantable lead in place.

2. The implantable lead of claim 1, wherein each electrode contact is positioned in a recess formed below the surface.

3. The implantable lead of claim 1, wherein the tether is integral with the paddle.

4. The implantable lead of claim 1, wherein the portion of the tether is embedded below the surface of the paddle.

5. The implantable lead of claim 1, wherein the portion of the tether substantially extends around a perimeter of the paddle and is positioned a distance from an edge of the paddle.

6. The implantable lead of claim 1, wherein the tether has two unattached ends that extend from one of the ends of the paddle.

7. The implantable lead of claim 1, wherein the electrode array comprises eight electrode contacts positioned in an array of rows and columns.

8. The implantable lead of claim 1, further comprising a securing device configured to receive at least one of the ends of the tether.

9. A method of implanting the implantable lead of claim 1 the method comprising:
   exposing a portion of a spinal cord;
   passing a suture beneath at least one of a lamina or a portion of a spine at a position near the exposed portion of the spinal cord;
   pulling, using the suture, the unattached end of the tether in a distal direction to insert the paddle into an epidural space of the spinal canal; and
   securing, using the tether, the lead in the epidural space.

10. The method of claim 9, wherein the securing comprises:
    making a hole in a spinous process;
    passing the unattached end of the tether through the hole; and
    tying the unattached end of the tether.

11. The method of claim 9, wherein the securing comprises tying the unattached end of the tether around a spinous process.

12. The method of claim 9, wherein the securing comprises:
    making a hole in a spinous process;
    inserting a securing device in the hole; and
    attaching the unattached end of the tether to the securing device.

13. The method of claim 9, wherein a portion of the tether substantially extends around a perimeter of the paddle and is positioned a distance from an edge of the paddle.

14. An implantable lead for electric stimulation of a spinal cord, comprising:
    a paddle sized to be positioned in the epidural space of the spinal canal and having a surface, a distal end and a proximal end, and a length that spans one vertebral level of the spinal cord;
    an electrode array positioned and arranged on the surface of the paddle, the electrode array comprising a plurality of electrode contacts each positioned in a recess formed below the surface of the paddle and configured to communicate with a corresponding electrode and a conductor; and at least one tether is having a portion that is connected to and positioned a distance from an edge of the paddle, extending around a perimeter of the paddle, and having an end that extends from and is unattached to the distal end of the paddle, wherein the tether is configured to pull the paddle in the epidural space.

15. The implantable lead of claim 14, wherein the portion of the tether is integral with the paddle.

16. The implantable lead of claim 14, wherein the portion of the tether is embedded below the surface of the paddle.

17. The implantable lead of claim 14, wherein the tether has two ends that extend from and are unattached to the distal end of the paddle.

18. The implantable lead of claim 14, further comprising a securing device configured to receive the unattached end of the tether.

19. A method of making an implantable lead configured for electric stimulation of a spinal cord, comprising:
   forming a paddle sized to be positioned in the epidural space of the spinal canal and having a surface, an end, a length that spans one vertebral level of the spinal cord, and at least one tether having a portion that is connected to the paddle and an end that is unattached to the paddle, wherein an electrode array is positioned and arranged on the surface of the paddle, the electrode array comprising at least one electrode contact configured to communicate with a corresponding electrode and a conductor, wherein the tether is configured to pull the paddle into the epidural space and secure the implantable lead in place.

20. The method according to claim 19, wherein each electrode contact is positioned in a recess formed below the surface of the paddle.

21. The method according to claim 19, wherein the portion of the tether is integral with the paddle.

22. The method of claim 19, wherein the portion of the tether is embedded below the surface of the paddle.

23. The method of claim 19, wherein the portion of the tether substantially extends around a perimeter of the paddle and is positioned a distance from an edge of the paddle.

24. A kit, comprising:
   an implantable lead for electrical stimulation of a spinal cord, comprising:
      a paddle sized to be positioned in the epidural space of the spinal canal and having a surface, a first and a second end, and a length that spans one vertebral level of the spinal cord;
      an electrode array positioned and arranged on the surface of the paddle, the electrode array comprising at least one electrode contact configured to communicate with a corresponding electrode and a conductor; and
      at least one tether having a portion that is connected to the paddle and an end that extends from and is attached to one of the ends of the paddle; and
   instructions for implanting the paddle into the epidural space of the spinal canal, wherein the tether is configured to pull the paddle into the epidural space and secure the implantable lead in place.

25. The kit of claim 24, wherein each electrode contact is positioned in a recess fanned below the surface.

26. The kit of claim 24, wherein the portion of the tether is integral with the paddle.

27. The kit of claim 24, wherein the portion of the tether substantially extends around a perimeter of the paddle and is positioned a distance from an edge of the paddle.

28. The kit of claim 24, further comprising a securing device configured to receive the unattached end of the tether.

* * * * *